US 9,814,583 B2

(12) United States Patent
Aquilo et al.

(10) Patent No.: US 9,814,583 B2
(45) Date of Patent: Nov. 14, 2017

(54) MODULAR STEM EXTENSION (75) Inventors: Dennis R. Aquilo, Winona Lake, IN (US); John E. Meyers, Columbia City, IN (US); Douglas G. Branscome, Fort Wayne, IN (US); Jack D. Jennings, Warsaw, IN (US); Abraham P. Habegger, Warsaw, IN (US); Alex P. Stoller, Fort Wayne, IN (US); Kelly A. Timmons, Warsaw, IN (US); Nathan Chastain, Warsaw, IN (US); Marvin Figueroa, Warsaw, IN (US); Clarence M. Panchison, Warsaw, IN (US); Gary D. Bos, Moxee, WA (US); Ernest U. Conrad, Seattle, WA (US); Kimberly Les, Clarkston, MI (US); Herrn Neumann, Magdeburg (DE); Mary I. O'Connor, Jacksonville, FL (US); Peter S. Walker, New York, NY (US); George D. Letson, Tampa, FL (US); Thomas P. Vail, San Francisco, CA (US)

(73) Assignee: Zimmer, Inc., Warsaw, IN (US)

( * ) Notice: Subject to any disclaimer, the term of this patent is extended or adjusted under 35 U.S.C. 154(b) by 1591 days.

(21) Appl. No.: 11/745,767

(22) Filed: May 8, 2007

(65) Prior Publication Data

US 2009/0222007 A1    Sep. 3, 2009

(51) Int. Cl.
*A61F 2/28* (2006.01)
*A61F 2/36* (2006.01)
(Continued)

(52) U.S. Cl.
CPC ........ *A61F 2/3609* (2013.01); *A61F 2/30734* (2013.01); *A61F 2/28* (2013.01);
(Continued)

(58) Field of Classification Search
CPC .... A61F 2002/2821; A61F 2002/30596; A61F 2002/30738; A61F 2002/4205;
(Continued)

(56) References Cited

U.S. PATENT DOCUMENTS 4,822,368 A * 4/1989 Collier .......................... 128/898
4,851,007 A    7/1989 Gray
(Continued)

FOREIGN PATENT DOCUMENTS

| EP | 1532945 A2 | 5/2005 |
| JP | 5507222 A | 10/1993 |
| WO | WO2006/065768 A2 | 6/2006 |

OTHER PUBLICATIONS

Surgical Technique—OSS Orthopaedic Salvage System, Femoral/Tibial Augmentation—Biomet Orthopedics, Inc. 2003-2004.
(Continued)

*Primary Examiner* — Ann Schillinger
(74) *Attorney, Agent, or Firm* — Schwegman Lundberg & Woessner, P.A.

(57) ABSTRACT

The modular stem component may include a shaft portion, a head, and a sleeve. The shaft portion is configured for receipt within the intramedullary canal of a bone and the head is configured to receive another component of a modular prosthetic system, such as a femoral neck, thereon. In one exemplary embodiment, the head extends radially around at least a portion of the stem and includes a rib defining a flange extending therefrom. The sleeve, which is formed as an independent part of the modular stem component and is made at least partially of a highly porous biomaterial, includes opposing ends and has a bore extending therethrough. The bore is configured to facilitate sliding receipt of the sleeve on the head.

18 Claims, 6 Drawing Sheets

(51) Int. Cl.
*A61F 2/30* (2006.01)
*A61F 2/46* (2006.01)

(52) U.S. Cl.
CPC ......... *A61F 2/30767* (2013.01); *A61F 2/3662* (2013.01); *A61F 2/4607* (2013.01); *A61F 2002/30006* (2013.01); *A61F 2002/30013* (2013.01); *A61F 2002/3054* (2013.01); *A61F 2002/3092* (2013.01); *A61F 2002/30126* (2013.01); *A61F 2002/30156* (2013.01); *A61F 2002/30217* (2013.01); *A61F 2002/30224* (2013.01); *A61F 2002/30327* (2013.01); *A61F 2002/30332* (2013.01); *A61F 2002/30341* (2013.01); *A61F 2002/30367* (2013.01); *A61F 2002/30382* (2013.01); *A61F 2002/30403* (2013.01); *A61F 2002/30405* (2013.01); *A61F 2002/30448* (2013.01); *A61F 2002/30449* (2013.01); *A61F 2002/30512* (2013.01); *A61F 2002/30604* (2013.01); *A61F 2002/30616* (2013.01); *A61F 2002/30738* (2013.01); *A61F 2002/30886* (2013.01); *A61F 2002/30981* (2013.01); *A61F 2002/3652* (2013.01); *A61F 2002/3656* (2013.01); *A61F 2002/4681* (2013.01); *A61F 2220/005* (2013.01); *A61F 2220/0025* (2013.01); *A61F 2220/0033* (2013.01); *A61F 2230/0008* (2013.01); *A61F 2230/0023* (2013.01); *A61F 2230/0067* (2013.01); *A61F 2230/0069* (2013.01); *A61F 2250/0015* (2013.01); *A61F 2250/0024* (2013.01); *A61F 2250/0039* (2013.01); *A61F 2310/00161* (2013.01); *A61F 2310/00491* (2013.01); *A61F 2310/00544* (2013.01)

(58) Field of Classification Search
CPC ... A61F 2002/4207; A61F 2002/30622; A61B 17/7032; A61B 17/7035; A61B 2017/564; A61B 5/4504
USPC .............................................. 623/22.11–23.5
See application file for complete search history.

(56) References Cited

U.S. PATENT DOCUMENTS

| | | | | |
|---|---|---|---|---|
| 4,995,883 | A * | 2/1991 | Demane et al. ........... | 623/22.42 |
| 5,019,103 | A * | 5/1991 | Van Zile et al. .......... | 623/20.34 |
| 5,658,349 | A * | 8/1997 | Brooks ............... | A61F 2/30739 623/23.23 |
| 5,876,459 | A * | 3/1999 | Powell ........................ | 623/23.15 |
| 6,214,052 | B1 * | 4/2001 | Burkinshaw .............. | 623/20.34 |
| 6,319,286 | B1 * | 11/2001 | Fernandez .......... | A61F 2/30734 623/16.11 |
| 6,447,549 | B1 * | 9/2002 | Taft .......................... | A61F 2/38 623/20.14 |
| 6,613,092 | B1 | 9/2003 | Kana et al. | |
| 6,824,566 | B2 | 11/2004 | Kana et al. | |
| 6,887,276 | B2 * | 5/2005 | Gerbec et al. ............ | 623/18.11 |
| 7,044,975 | B2 * | 5/2006 | Cheal et al. ............... | 623/22.42 |
| 7,842,093 | B2 * | 11/2010 | Peters et al. .............. | 623/20.15 |
| 2004/0107001 | A1 | 6/2004 | Cheal et al. | |
| 2004/0117024 | A1 | 6/2004 | Gerbec et al. | |
| 2005/0143837 | A1 | 6/2005 | Ferree | |

OTHER PUBLICATIONS

The European Search Report dated Sep. 11, 2008, in related European Application No. EP08251518.0.
The European Office Action dated Jun. 4, 2009, in related European Application No. EP08251518.0.
"Canadian Application Serial No. 2,626,494, Office Action dated Mar. 13, 2014", 2 pgs.
"Japanese Application Serial No. 2008-122510, Office Action dated Nov. 13, 2012", (English Translation), 3 pgs.
"Japanese Application Serial No. 2008-122510, Response filed Feb. 13, 2013 to Office Action dated Nov. 13, 2012", (W/ English Translation), 14 pgs.
"European Application Serial No. 08251518.0, Examination Notification Art. 94(3) dated Mar. 12, 2015", 5 pgs.
"European Application Serial No. 08251518.0, Communication Pursuant to Article 94(3) EPC dated Jun. 4, 2009", 2 pgs.
"European Application Serial No. 08251518.0, Communication Pursuant to Article 94(3) EPC dated Aug. 8, 2016", 5 pgs.
"European Application Serial No. 08251518.0, Extended European Search Report dated Oct. 8, 2008", 7 pgs.
"European Application Serial No. 08251518.0, Response filed Sep. 22, 2015 to Communication pursuant to Article 94(3) EPC dated Mar. 12, 2015", 9 pgs.
"European Application Serial No. 08251518.0, Response filed Oct. 14, 2009 to Communication pursuant to Article 94(3) EPC dated Jun. 4, 2009", 8 pgs.
"European Application Serial No. 08251518.0, Communication Pursuant to Article 94(3) EPC dated Feb. 14, 2014", 7 pgs.
"European Application Serial No. 08251518.0, Response filed Dec. 19, 2016 to Communication Pursuant to Article 94(3) EPC dated Aug. 8, 2016", 10 pgs.
"European Application Serial No. 08251518.0, Response dated Aug. 24, 2017 to Communication Pursuant to Article 94(3) EPC dated Feb. 14, 2017", 23 pgs.

* cited by examiner

FIG_3

FIG_4

FIG_5

FIG_6

FIG_7

FIG_8

FIG_9

FIG_10

FIG_11

MODULAR STEM EXTENSION

BACKGROUND

1. Field of the Invention

The present invention relates to orthopedic implants and, particularly, to modular orthopedic components.

2. Description of the Related Art

To repair diseased and/or damaged bone, orthopedic implants may be utilized. Orthopedic implants are designed to replace the diseased and/or damaged bone and to replicate the anatomy of the same. Thus, when a bone becomes diseased and/or damaged, such as a femur, the diseased and/or damaged portion of the bone may be osteotomized. An implant, replicating the function of the osteotomized bone, may then be implanted. For example, when the head of a femur becomes diseased and/or damaged, the same may be resected and a stem implanted within the intramedullary canal of the femur. The stem may include an integral head configured to replicate the function of the osteotomized natural femoral head or, alternatively, the stem may be one component of a modular prosthesis system. To help retain the stem in its proper position, the head of the stem may be formed to include porous surfaces that facilitate tissue ingrowth. These porous surfaces may be located at a position on the head of the stem that is separated from the surface of the osteotomized bone.

SUMMARY

The present invention relates to orthopedic implants and, particularly, to modular orthopedic components. In one exemplary embodiment, a modular stem component is provided and may include a shaft portion, a head, and a discrete sleeve. The shaft portion of the stem is configured for receipt within the intramedullary canal of a bone and the head of the stem is configured to extend above the osteotomized bone. The head of the stem may also receive another component of a modular prosthetic system, such as a femoral neck, thereon. In one exemplary embodiment, the sleeve, which is formed as an independent component and is made at least partially of a highly porous biomaterial, is dimensioned to be received on the exterior of the head of the stem. With the sleeve received on the head of the stem, implantation of the shaft portion within the intramedullary canal of a bone results in the sleeve directly contacting the osteotomized bone to facilitate boney ingrowth and further secure the stem component within the intramedullary canal of the bone. For example, in one embodiment, the sleeve is captured between the resected bone and a flange extending from the head of the stem. In another exemplary embodiment, the sleeve is retained on the head of the stem by a taper lock or adhesive, for example.

Advantageously, by forming the sleeve as an independent part of the modular stem component, the shaft portion and head of the stem may be formed and prepared without the need to protect the highly porous biomaterial forming the sleeve. Thus, the number of masks and the amount of special fixturing used during production are substantially decreased. As a result, the cost of manufacturing the modular stem component is correspondingly reduced. Additionally, due to the sleeve being at least partially formed from a highly porous biomaterial, the sleeve facilitates bony ingrowth and osteointegration of the bone with the modular stem component. This boney ingrowth may help to seal the intramedullary canal of the bone in which the shaft portion is implanted and provide additional stability to the head of the stem. Further, the interaction between the sleeve and the bone helps to prevent pistoning of the stem within the intramedullary canal of the bone and eliminates the need to drill stability holes in the bone to prevent rotation of the stem.

In one form thereof, the present invention provides a modular prosthetic component configured for implantation within a bone, the modular prosthetic component including: a stem having an elongate shaft portion defining a longitudinal axis; a head extending from said stem, said head having a stop; and a sleeve dimensioned for receipt on said head, said sleeve formed at least partially from a highly porous biomaterial, said highly porous biomaterial allowing tissue ingrowth therein, said sleeve having an exterior surface, an interior surface defining an internal bore, and opposing ends connecting said exterior surface and said interior surface, said sleeve dimensioned for sliding receipt on said head in a first direction, wherein said stop limits movement of said sleeve in the first direction, whereby said sleeve is captured by said stop and the bone when said stem is implanted in the bone.

In another form thereof, the present invention provides a modular prosthetic component configured for implantation within a bone, the modular prosthetic component including: a stem having a shaft portion defining a longitudinal axis; a head having a throughbore formed therein, said throughbore dimensioned to receive at least a portion of said stem therein; and a plurality of sleeves having different dimensions, each of said plurality of sleeve formed at least partially from a highly porous biomaterial and configured for interchangeable receipt on said head.

In yet another form thereof, the present invention provides a method of implanting a modular prosthetic component having a head and a stem, including the steps of: positioning a sleeve formed at least partially from a highly porous biomaterial on the head interoperatively; implanting at least a portion of the stem in the intramedullary canal of a bone; and seating the stem to provide direct contact between an end of the sleeve and the bone.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figures 1, 2:
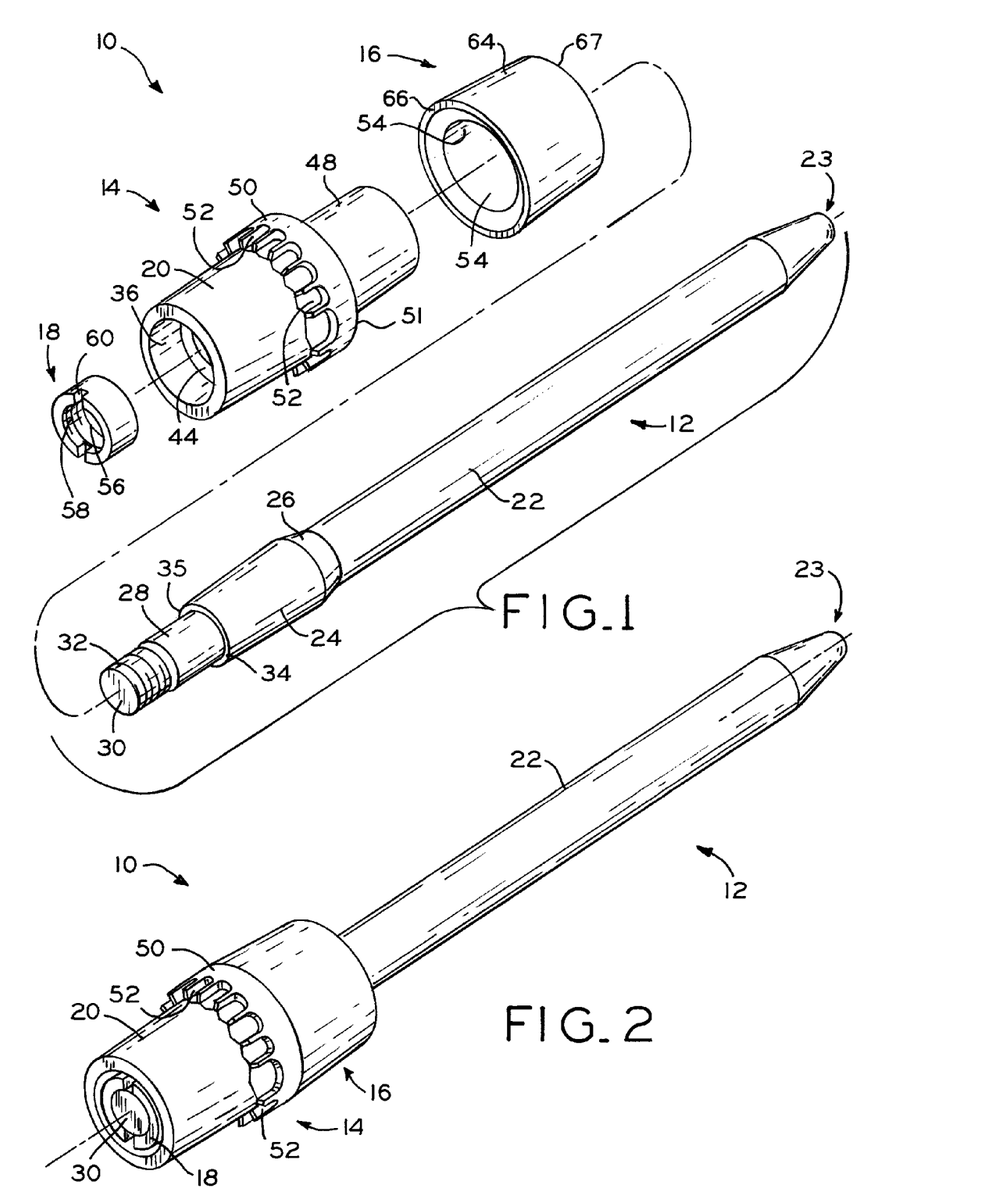
FIG. 1 is an exploded view of a stem, a head, and a sleeve according to one embodiment of the present invention.
FIG. 2 is a perspective view of the stem, head, and sleeve of FIG. 1.
Figure 3:
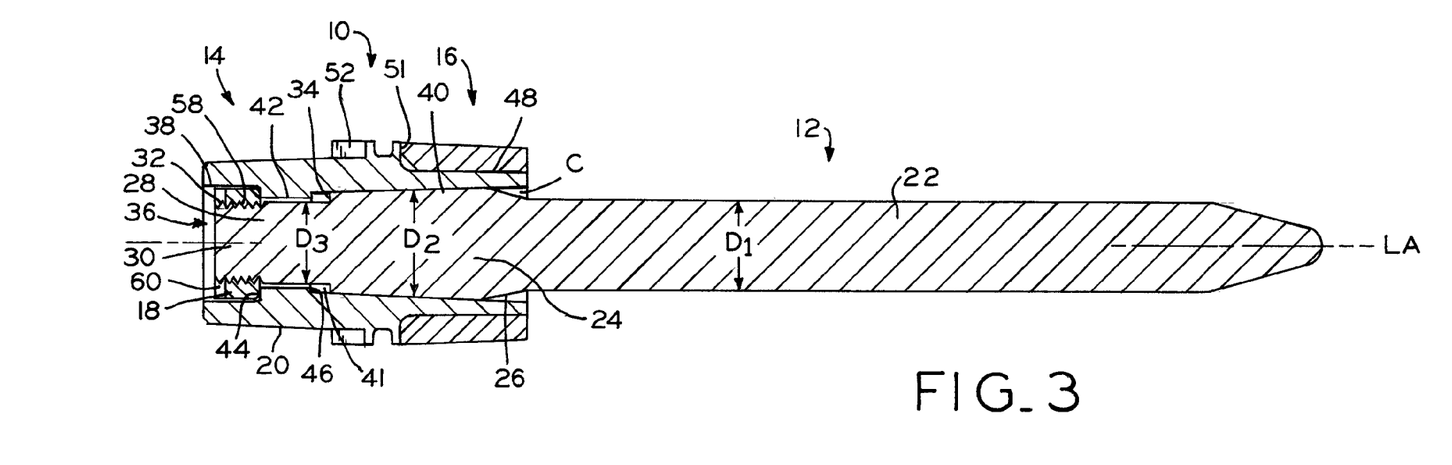
FIG. 3 is a cross-sectional view of the stem, head, and sleeve of FIG. 2 taken along line 3-3 of FIG. 2.

Referring to FIGS. 1-3, modular stem component 10, which is one component of a modular prosthesis system, includes stem 12, head 14, sleeve 16, and nut 18. Modular stem component 10 may be connected to another component of the modular prosthesis system through mating engagement with tapered surface 20 of head 14. For example, in a proximal femoral modular prosthesis system, a femoral neck (not shown) having a corresponding female tapered surface may be secured to head 14 via engagement with male tapered surface 20. The neck may be configured to receive an additional component of the modular prosthesis system, such as a femoral head (not shown), thereon. Additionally, sleeve 16 may be received on head 14. Once assembled, stem portion 12 of modular component 10 may be implanted into the intramedullary canal of a bone, allowing sleeve 16 to directly contact the osteotomized surface of the bone.

Referring to FIGS. 1 and 3, stem 12 includes shaft portion 22 and head engagement portion 24. Shaft portion 22 has a diameter $D_1$ (FIG. 3) and head engagement portion 24 has a diameter $D_2$ (FIG. 3), which is greater than diameter $D_1$ of shaft portion 22. Formed between diameters $D_1$, $D_2$ of shaft portion 22 and head engagement portion 24, respectively, is tapered shoulder 26. Extending from head engagement portion 24, in a direction opposite shaft portion 22, is post 28. Post 28 includes end 30 having threads 32 extending therefrom. Threads 32 provide for mating engagement of post 28 with nut 18, as described below. Additionally, threads 32 may facilitate the implantation and extraction of stem 12 by providing for mating engagement between post 28 and a taper seating tool (not shown) and between post 28 and a slap hammer attachment (not shown), respectively. Diameter $D_3$ (FIG. 3) of post 28 is less than diameter $D_2$ of head engagement portion 24, which results in the formation of shoulder 34 therebetween. Shoulder 34 includes flat 35 (FIG. 1) configured to align with a corresponding flat on head 14, described in detail below.

Nut 18 of modular stem component 10 is configured for receipt on post 28 of stem 12. Specifically, the internal surface of nut 18 defines bore 56 having threads 58 extending therefrom. Threads 58 are dimensioned to threadingly engage threads 32 extending from post 28 of stem 12. Additionally, impaction slots (not shown) may be formed in end 30 of stem 12 and may align be aligned with slots 60 formed in nut 18. Impaction slots (not shown) may be dimensioned to matingly engage an impaction tool (not show) and facilitate the impaction of stem 12 into the intramedullary canal of a bone, as described in detail below.

As stated above, modular prosthesis 10 also includes head 14. Extending through head 14 is internal bore 36. Referring to FIG. 3, internal bore 36 includes counterbored portion 38 and stem engagement portion 40, which are separated from one another by smaller diameter portion 42. Stem engagement portion 40 includes flat 41 configured to align with flat 35 of stem 12. Flats 35, 41 are formed on the annular surfaces of shoulder 34 and stem engagement portion 40, respectively, and must be aligned in order to seat head engagement portion 24 and stem engagement portion 40, as described in detail below. Advantageously, the interaction of flats 35, 41 also prevent rotation of stem 12 relative to head 14 and, resultantly, helps to lessen the potential for loosening of stem 12 and head 14 under torsional loads. Defined between smaller diameter portion 42 and counterbored portion 38 is shoulder 44. Similarly, defined between smaller diameter portion 42 and stem engagement portion 40 is shoulder 46. As described in detail below, stem engagement portion 40 of internal bore 36 is dimensioned to receive and engage head engagement portion 24 of stem 12 therein.

Figure 5:
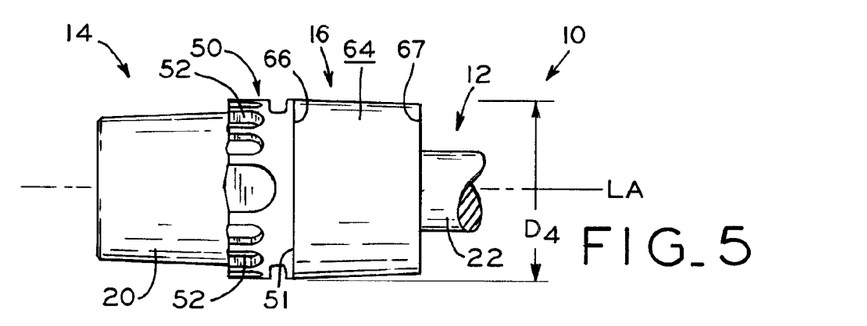
FIG. 5 is a fragmentary, side view of the stem, head, and sleeve of FIG. 3.

The exterior of head 14 includes tapered surface 48 separated from tapered surface 20 by flange 50. Referring to FIG. 5, flange 50 has a diameter $D_4$ and includes a plurality of indentations 52 formed therein. Indentations 52 extend from tapered surface 20 and into flange 50. Indentations 52 are configured to receive corresponding tabs extending from an additional modular prosthetic component, such as a femoral neck (not shown). The interaction of indentations 52 with the tabs of an additional modular femoral component allows for fixed adjustment of the rotational position of the additional modular prosthetic component. Further, by allowing the surgeon to adjust the rotational position of the modular prosthetic components with respect to one another, the kinematics of the joint may be adjusted, the implant stress lessened, and joint stability enhanced.

Figure 4:
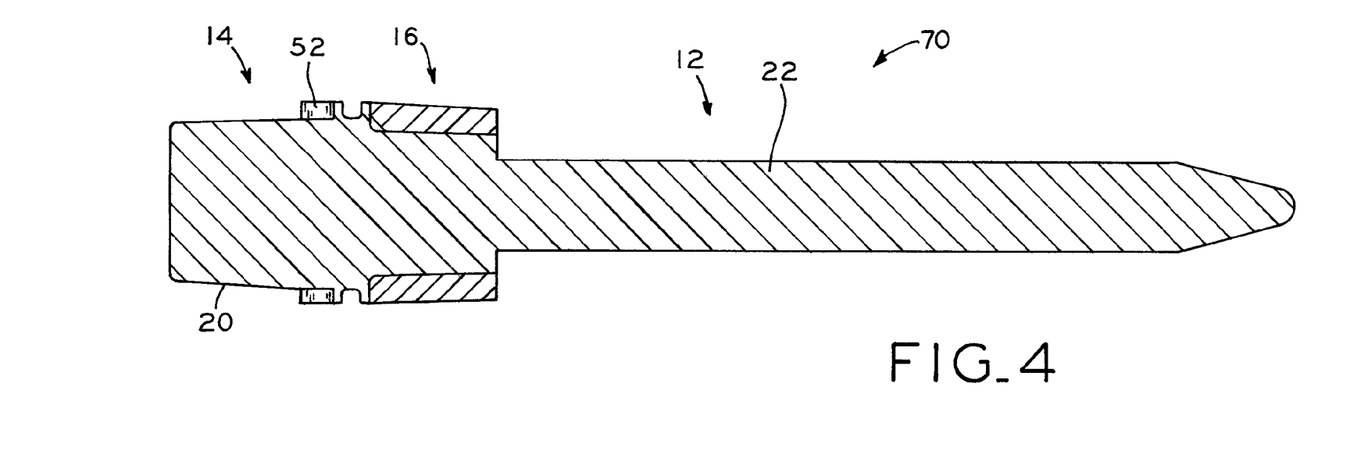
FIG. 4 is a cross-sectional view of another exemplary embodiment of the stem, head, and sleeve, depicting the stem and head integrally formed.

In another exemplary embodiment of modular stem component 10, shown in FIG. 4 as modular component 70, head 14 and stem 12 are formed as a single, integral component. In this embodiment, head 14 extends radially around stem 12 in a manner substantially similar to that of modular stem component 10. As described and depicted herein, modular component 70 has several features that are identical or substantially identical to modular stem component 10, and identical reference numerals have been used to indicate identical or substantially identical components therebetween.

Figure 13:
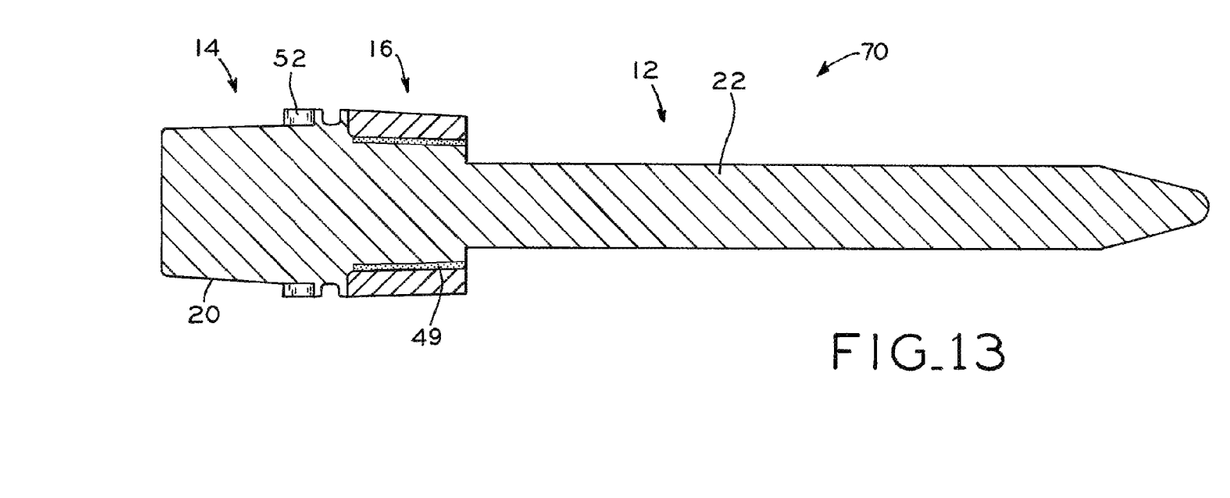
FIG. 13 is a cross-sectional view similar to FIG. 4 depicting the sleeve adhesively retained on the head.

Sleeve 16 of modular stem component 10 is configured for receipt on exterior tapered surface 48 of head 14. Specifically, internal surface 54 of sleeve 16 defines internal bore 53 dimensioned for receipt on tapered surface 48. In one exemplary embodiment, internal bore 53 is dimensioned such that inner surface 54 matingly engages tapered surface 48 of head 14 (FIG. 4). For example, inner surface 54 of sleeve 16 may be correspondingly tapered to lock sleeve 16 on tapered surface 48. In another exemplary embodiment, sleeve 16 may be retained on tapered surface 48 of head 14 by an adhesive 49 (FIG. 13). By utilizing an adhesive 49, such as bone cement, a resin, or another biocompatible slip resistant material, the need to heat treat head 14 to secure sleeve 16 thereto is eliminated. Additionally, in another exemplary embodiment, surface 48 may be design to increase friction between surface 48 and sleeve 16 to facilitate the retention of sleeve 16 thereon. For example, surface 48 may be knurled, have at least one dimple formed thereon, or have a polymethylmethacrylate coating.

In another exemplary embodiment, a plurality of sleeves 16 may be provided with the modular prosthesis system, each having different dimensions, which may correspond to sleeves 71 (FIG. 7), 80 (FIG. 8), 90 (FIG. 9), 100 (FIG. 10), 120 (FIG. 11), 130 (FIG. 12) for example. By providing the surgeon with a plurality of sleeves 16, the surgeon may select the one of the plurality of sleeves 16 that is preferable for an individual patient. Additionally, by forming sleeve 16 as an independent component, the number of masks and amount of special fixturing used during production of modular stem component 10 are substantially reduced. Specifically, during manufacturing the need to mask or otherwise protect sleeve 16 is substantially eliminated. As a result, the cost of manufacturing modular stem component 10 is decreased.

Figure 6:
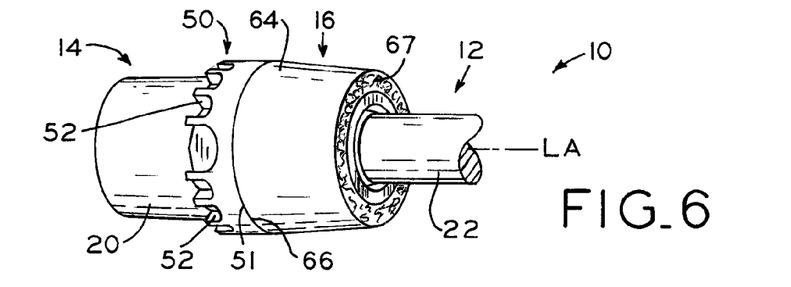
FIG. 6 is a fragmentary perspective view of the stem, head, and sleeve of FIG. 2.

Referring FIGS. 5 and 6, exterior surface 64 of sleeve 16 has a slight taper in the direction of shaft portion 22 of stem 12. Additionally, sleeve 16 further includes opposing end surfaces 66, 67. In one exemplary embodiment, sleeve 16 is configured for sliding receipt on tapered surface 48 of head 14 in the direction of flange 50. Specifically, sleeve 16 may be received on tapered surface 48 of head 14 and advanced along longitudinal axis LA of stem 12 until end surface 66 contacts flange 50. The interaction between end surface 66 of sleeve 16 and flange 50 of head 14 prevents further translation of sleeve 16 along longitudinal axis LA of stem 12 in the direction of flange 50.

Figure 11:
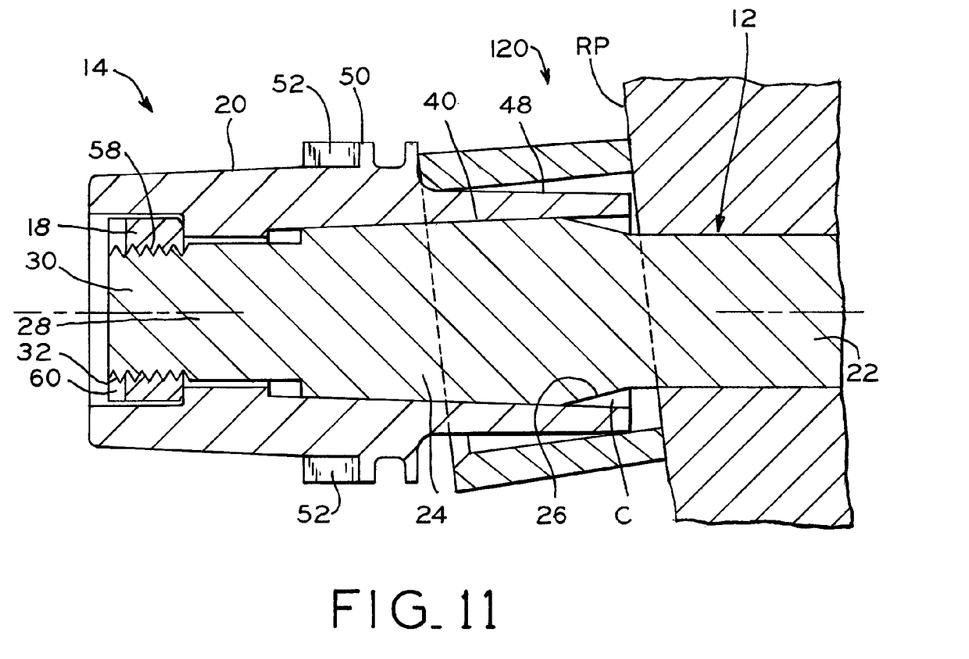
FIG. 11 is a fragmentary cross-sectional view of the stem and head of FIG. 9, further depicting a sleeve according to another exemplary embodiment.

In one exemplary embodiment, internal bore 53 of sleeve 16 may be dimensioned such that, when sleeve 16 is positioned over head 14, a gap is formed between inner surface 54 of sleeve 16 and exterior tapered surface 48 of head 14. In this embodiment, sleeve 16 may be canted relative to head 14 when modular stem component 10 is finally implanted. For example, as shown in FIG. 11, sleeve 120 has a internal diameter, which is greater then the external diameter of tapered surface 48 of head 14 and less then diameter $D_4$ (FIG. 5) of flange 50 of head 14. As a result, sleeve 120 may tilt or cant relative to longitudinal axis LA of stem 12 and relative to head 14, but cannot pass over flange 50. Advantageously, this allows for sleeve 120 to be fully seated on the resected bone surface, i.e., the entire circumference of sleeve 120 rests against the resected bone surface, as described in detail below, and captured between flange 50 and the resected bone, even when resection plane RP is not perpendicular to longitudinal axis LA of stem 12.

Sleeve 16 is made at least in part of, and may be made entirely of, a highly porous biomaterial useful as a bone substitute and/or cell and tissue receptive material. A highly porous biomaterial may have a porosity as low as 55, 65, or 75 percent and as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of tissue, such as cancellous bone, through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which tissue, such as cancellous bone, may grow to provide fixation of sleeve 16 to the surrounding bone, as described below.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

With sleeve 16 received on head 14, as described in detail above, stem 12 may be inserted within internal bore 36 of head 14. Specifically, threaded end 30 of stem 12 may be inserted within internal bore 36 and advanced in the direction of counterbored portion 38, allowing head 14 to extend radially around at least a portion of stem 12. With stem 12 advanced toward counterbored portion 38, head engagement portion 24 of stem 12 may contact stem engagement portion 40 of head 14. In one exemplary embodiment, head engagement portion 24 and stem engagement portion 40 form corresponding male and female tapers, respectively. Thus, as stem 12 is advanced within internal bore 36, the engagement of the corresponding tapers of head engagement portion 24 and stem engagement portion 40 substantially prevent additional advancement of stem 12 therethrough.

Once stem 12 is positioned within internal bore 36 of head 14, nut 18 is received within counterbored portion 38 of internal bore 36 and threadingly engaged with post 28. Specifically, threads 58 of nut 18 threadingly engage threads 32 of post 28. As nut 18 is threadingly advanced via a tool (not shown), which may also engage slots 60, nut 18 seats against flange 44 and provides a securement mechanism to prevent migration of stem 12 from internal bore 36. With stem 12 properly seated within bore 36, clearance C, shown in FIG. 3, is formed between stem 12 and stem engagement portion 40 of head 14. Advantageously, clearance C increases the strength of modular stem component 10 by reducing the stresses in head 14.

Once stem 12, head 14, sleeve 16, and nut 18 are secured to one another to form modular stem component 10, the bone is resected to remove the diseased or damaged portion and modular stem component 10 is inserted within the intramedullary canal of the bone and impacted. Alternatively, the bone may be resected prior to the assembly of stem 12, head 14, sleeve 16, and nut 18 to form modular stem component 10. Specifically, to implant modular component 10, nose 23 (FIG. 1) of stem 12 is inserted within the intramedullary canal of the bone and stem 12 impacted to seat the same therein. The impaction of stem 12 may be facilitated by the use of an impaction tool (not shown) configured to mate with impaction slots (not shown) in stem 12 and with slots 60 in nut 18. Additionally, in one exemplary embodiment, end 30 of stem 12 also include impaction slots (not shown) formed therein. The impaction slots formed in stem 12 may indicate the orientation of stem landmarks which may not be visible during impaction. Stem 12 is impacted until end 67 of sleeve 16 is seated adjacent to the bone. In one exemplary embodiment, stem 12 is impacted until end 67 of sleeve 16 directly contacts the bone. In another exemplary embodiment, the cross-section of sleeve 16 at end 67 is non-cylindrical. For example, the cross-section of sleeve 16 at end 67 may be triangular, elliptical, or oval.

Advantageously, due to sleeve 16 being at least partially constructed from a highly porous biomaterial, sleeve 16 facilitates bony ingrowth and osteointegration of the bone with modular stem component 10. This boney ingrowth and osteointegration may help to seal the intramedullary canal of the bone in which stem 12 is inserted and provide additional stability to head 14. Further, the interaction between sleeve 16 and the resected end of the bone helps to prevent pistoning of stem 12 within the intramedullary canal of the bone and eliminates the need to drill stability holes in the bone to prevent rotation of stem 12.

Figure 7:
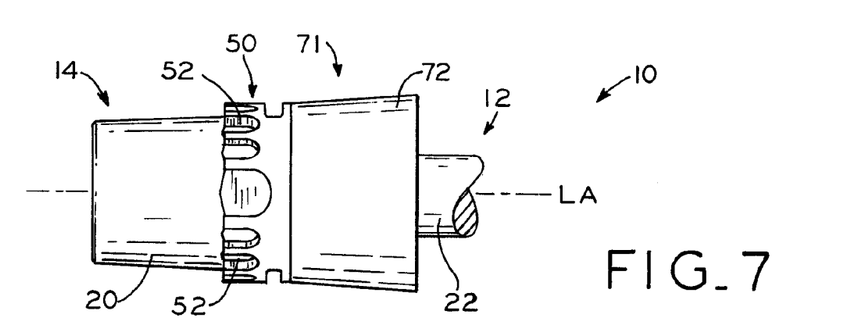
FIG. 7 is a fragmentary side view of the stem and head of FIG. 3, further depicting a sleeve according to another exemplary embodiment.
Figure 8:
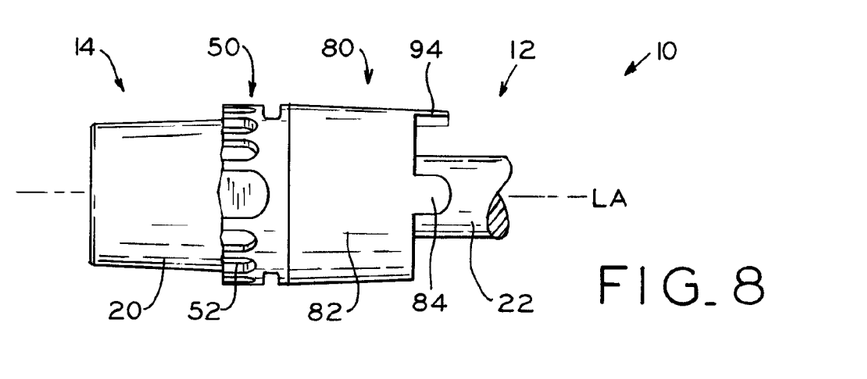
FIG. 8 is a fragmentary side view of the stem and head of FIG. 3, further depicting a sleeve according to another exemplary embodiment.

FIGS. 7-10 depict other exemplary embodiments of sleeve 16 as sleeves 71, 80, 90, and 100, respectively. Sleeves 71, 80, 90, and 100 have several features that are identical or substantially identical, such as being constructed at least partially of a highly porous biomaterial, to corresponding features of sleeve 16 of FIG. 1 and identical reference numerals have been used to identify identical or substantially identical features therebetween. Referring to FIG. 7, sleeve 71 includes exterior surface 72 tapered in the direction of rib 50. Thus, exterior surface 72 of sleeve 70 has a taper opposite that of exterior surface 64 of sleeve 16. Referring to FIG. 8, exterior surface 82 of sleeve 80 includes tabs 84 extending therefrom which may extend past resection plane RP (FIG. 11) or be received within openings in the bone when stem 12 is implanted therein.

Figure 9:
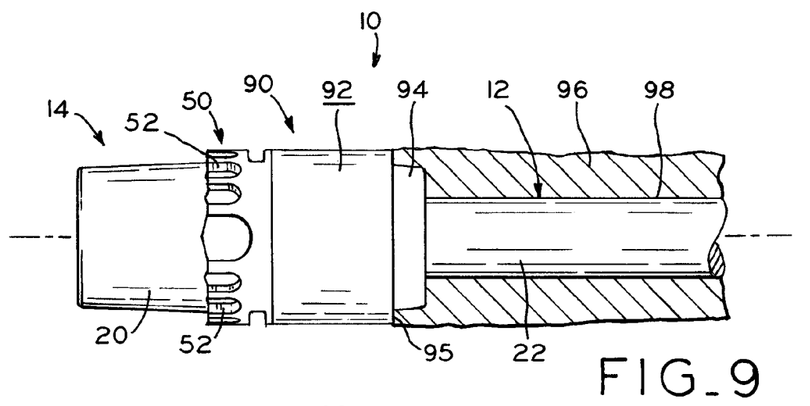
FIG. 9 is a fragmentary side view of the stem and head of FIG. 3, further depicting a sleeve according to another exemplary embodiment and further depicting the stem received within the intramedullary canal of a femur.

Referring to FIG. 9, sleeve 90 includes exterior surface 92 having a first diameter and stepped portion 94 having a second diameter. As shown in FIG. 9, the diameter of stepped portion 94 is less than the diameter of exterior surface 92. In this embodiment, stepped portion 94 is configured to be received within a portion of a bone, such as femur 96. Thus, prior to insertion of stem 12, femur 96 is shaped to receive stepped portion 94 therein. Upon insertion of stem 12 within intramedullary canal 98 of femur 96, stepped portion 94 and flange 95 contact femur 96 to facilitate boney ingrowth and osteointegration of femur 96 with sleeve 90.

Figure 10:
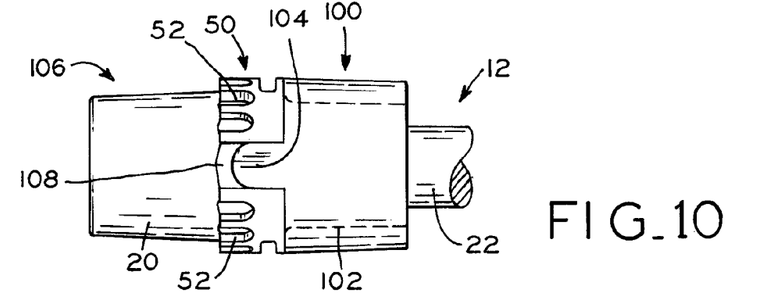
FIG. 10 is a fragmentary, side view of the stem of FIG. 3, further depicting a head and a sleeve according to another exemplary embodiment.

FIG. 10 depicts yet another embodiment of sleeve 16 as sleeve 100. Sleeve 100 includes exterior surface 102 having tabs 104 extending therefrom. Tabs 104 are configured for receipt within slots 108 formed in flange 50 of head 106. Head 106 has several features that are identical or substantially identical to corresponding features of head 14 of FIG. 1 and identical reference numerals have been used to identify identical or substantially identical features therebetween. By receiving tabs 104 within slots 108, head 106 prevents rotation of sleeve 100 relative thereto.

Figure 12:
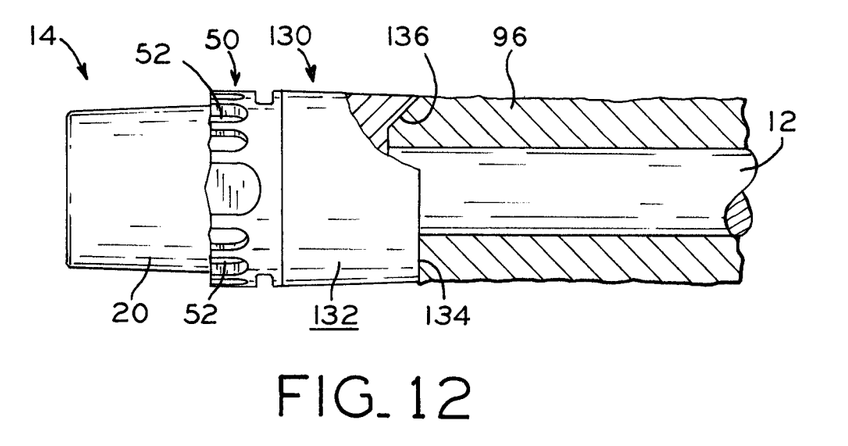
FIG. 12 is a fragmentary, cross-sectional side view of stem and head of FIG. 3, further depicting a sleeve according to another exemplary embodiment.

FIG. 12 depicts a further embodiment of sleeve 16 as sleeve 130. Sleeve 130 includes exterior 132 and bone contacting surface 134. Bone contacting surface 134 includes chamfered portion 136, shown in partial cross-section in FIG. 12, extend substantially entirely along exterior 132 of sleeve 130. Chamfered portion 136 of sleeve 130 is configured to facilitate contact with resected bone and allow for seating of sleeve 130 on the bone, such as femur 96. Additionally, the use of chamfered portion 136 substantially prevents canting of sleeve 130 relative to head 14 and stem 12.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A modular prosthetic component configured for implantation within a bone, the modular prosthetic component comprising:
    a stem having a proximal end and a distal end and including an elongate shaft portion defining a longitudinal axis, wherein the distal end of the stem includes a distal leading tip for leading the stem into the bone when implanting the stem in the bone;
    a head extending from said stem at the proximal end of the stem, said head including a first end and a second end with a flange extending circumferentially around the head between said first end and said second end, wherein the head is oriented with respect to the stem such that the second end of the head is situated between the first end of the head and the distal end of the stem, and wherein the first end of said head includes a tapered exterior surface for mating engagement with a second modular component; and
    a sleeve dimensioned for receipt on the second end of said head, said sleeve formed at least partially from a highly porous biomaterial, said porous biomaterial allowing tissue in growth therein, said sleeve having an exterior surface, an interior surface defining an internal bore into which the second end of the head can be received, and first and second opposing ends connecting said exterior surface and said interior surface, said sleeve dimensioned for sliding receipt on an exterior surface of the second end of said head in a first longitudinal direction, wherein said flange separates the tapered exterior surface from the second end and is sized to limit movement of the sleeve in said first longitudinal direction so that the sleeve can be captured by the flange and a bone when said stem is implanted in the bone;
    wherein said head extends radially around said shaft portion of said stem, and wherein said flange defines a first diameter, and said sleeve further comprising opposing end surfaces, said internal bore of said sleeve having a second diameter that is less than said first diameter, wherein the receipt of said sleeve on the exterior surface of the second end of said head results in one of said opposing ends of said sleeve contacting said flange of said head to prevent further sliding of said sleeve in the direction toward the first end of said head and the other one of said opposing ends of said sleeve contacting the bone when said stem is implanted in the bone.

2. The modular prosthetic component of claim 1, wherein said stem and said head form an integral, monolithic component.

3. The modular prosthetic component of claim 1, wherein said stem and said head are individual, distinct components matingly engageable with one another.

4. The modular prosthetic component of claim 1, wherein said porous biomaterial has a porosity no lower than 75 percent.

5. The modular prosthetic component of claim 1, wherein said exterior surface of the second end of said head is tapered and said internal bore of said sleeve is tapered for taper locking the sleeve to the head.

6. The modular prosthetic component of claim 1, wherein the first end of said head and the second end of said head share a common central longitudinal axis.

7. The modular prosthetic component of claim 6, further comprising a plurality of additional sleeves having different dimensions than said sleeve, each of said plurality of additional sleeves dimensioned for receipt on the second end of said stem, each of said plurality of additional sleeves having an exterior surface, an interior surface defining an internal bore into which the second end of the head can be received, and opposing ends connecting said exterior surface and said interior surface, said internal bore of each of said plurality of additional sleeves having a second diameter that is less than an external surface diameter of said flange, each of said plurality of additional sleeves dimensioned for sliding receipt on the exterior surface of the second end of said head in a first direction, wherein the individual receipt of any sleeve selected from said plurality of additional sleeves on the second end of said head results in one of said opposing ends of said sleeve contacting said flange of said head to prevent further sliding of said sleeve in the first direction and the other one of said opposing ends of said sleeve contacting the bone when said stem is implanted in the bone.

8. The modular prosthetic component of claim 6, wherein the tapered exterior surface of the first end of said head has a maximum diameter that is greater than a maximum diameter of the exterior surface of the second end of said head.

9. The modular prosthetic component of claim 1, wherein said stem further includes a head engagement portion and said head further includes a stem engagement portion configured to matingly engage said head engagement portion, wherein the mating engagement between said head engagement portion and said stem engagement portion facilitates securement of said head to said stem.

10. The modular prosthetic component of claim 9, wherein said head engagement portion comprises a male taper and said stem engagement portion comprises a female taper for taper locking the head to the stem.

11. The modular prosthetic component of claim 1, wherein at least one of said opposing ends of said sleeve has a non-cylindrical cross-section.

12. The modular prosthetic component of claim 1, wherein an inner diameter of said sleeve exceeds an outer diameter of at least a portion of said head, whereby said sleeve is tiltable relative to said head and relative to the longitudinal axis of the elongate shaft portion of said stem.

13. The modular prosthetic component of claim 1, wherein said sleeve is secured to the exterior surface of the second end of said head by a biocompatible adhesive.

14. The modular prosthetic component of claim 1, wherein the flange extends radially around a full circumference of the head.

15. A modular prosthetic component configured for implantation within a bone, the modular prosthetic component comprising:
a stem having a shaft portion defining a longitudinal axis;
a head including a first end and a second end with a flange extending circumferentially around the head between said first end and said second end, wherein the first end of said head includes a tapered exterior surface for mating engagement with a second modular component, and wherein said head has a throughbore formed therein, said throughbore dimensioned to receive at least a portion of said stem therein; and
a sleeve formed at least partially from a highly porous biomaterial, the sleeve having an internal bore configured for receipt on an exterior surface of the second end of said head, the exterior surface of the second end of said head having a maximum diameter that is less than a maximum diameter of the tapered exterior surface of the first end of said head, wherein said flange separates the tapered exterior surface from the second end and is sized to limit movement of said sleeve on the exterior surface of the second end of said head in a direction toward the first end of said head;
wherein said head extends radially around said shaft portion of said stem, and wherein said flange defines a first diameter, and said sleeve further comprising opposing end surfaces, said internal bore of said sleeve having a second diameter that is less than said first diameter, wherein the receipt of said sleeve on the exterior surface of the second end of said head results in one of said opposing ends of said sleeve contacting said flange of said head to prevent further sliding of said sleeve in the direction toward the first end of said head and the other one of said opposing ends of said sleeve contacting the bone when said stem is implanted in the bone.

16. The modular prosthetic component of claim 15, wherein said head includes a slot formed therein and said sleeve includes a tab extending therefrom, said tab dimensioned for receipt within said slot, whereby receipt of said tab in said slot restricts rotation of said sleeve about said head.

17. The modular prosthetic component of claim 15, wherein said sleeve is tiltable relative to said head and relative to the longitudinal axis of the shaft portion of said stem.

18. The modular prosthetic component of claim 15, further comprising a plurality of additional sleeves having different dimensions than said sleeve, each of said plurality of additional sleeves formed at least partially from a porous biomaterial and dimensioned for receipt on said shaft portion of said stem.

* * * * *